United States Patent
Ouchi

(10) Patent No.: US 7,683,778 B2
(45) Date of Patent: Mar. 23, 2010

(54) APPARATUS FOR DETECTING INFORMATION ON OBJECT

(75) Inventor: Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 431 days.

(21) Appl. No.: 11/703,122

(22) Filed: Feb. 7, 2007

(65) Prior Publication Data

US 2007/0195921 A1    Aug. 23, 2007

(30) Foreign Application Priority Data

Feb. 15, 2006    (JP) .............................. 2006-037765

(51) Int. Cl.
G01F 23/284    (2006.01)
(52) U.S. Cl. .................... 340/539.1; 250/358.1; 324/96
(58) Field of Classification Search .............. 250/338.1, 250/330, 339.06, 341.1, 334; 324/96; 280/735; 310/300; 340/539.1
See application file for complete search history.

(56) References Cited

U.S. PATENT DOCUMENTS

| | | | |
|---|---|---|---|
| 5,586,131 A | 12/1996 | Ono et al. | |
| 5,659,560 A | 8/1997 | Ouchi et al. | |
| 5,699,373 A | 12/1997 | Uchida et al. | |
| 5,710,430 A | 1/1998 | Nuss | 250/358.1 |
| 5,764,670 A | 6/1998 | Ouchi | |
| 5,789,750 A | 8/1998 | Nuss | 250/358.1 |
| 6,084,939 A * | 7/2000 | Tamura | 378/98.2 |
| 6,854,901 B1 | 2/2005 | Ouchi | |
| 6,909,094 B2 * | 6/2005 | Tran et al. | 250/341.1 |
| 6,957,099 B1 * | 10/2005 | Arnone et al. | 600/473 |
| 7,062,116 B2 | 6/2006 | Ouchi | |
| 7,119,339 B2 * | 10/2006 | Ferguson et al. | 250/358.1 |
| 7,248,995 B2 | 7/2007 | Itsuji et al. | |
| 2004/0191945 A1 * | 9/2004 | Yamaguchi et al. | 438/48 |
| 2006/0039431 A1 | 2/2006 | Sekiguchi et al. | |
| 2006/0085160 A1 | 4/2006 | Ouchi | |
| 2006/0188398 A1 | 8/2006 | Yano et al. | |
| 2006/0197021 A1 | 9/2006 | Ouchi | |

(Continued)

FOREIGN PATENT DOCUMENTS

JP    2004-85359    3/2004

OTHER PUBLICATIONS

U.S. Appl. No. 11/632,958, filed Jan. 19, 2007, Inventor(s) T. Ouchi.

(Continued)

*Primary Examiner*—Daniel Wu
*Assistant Examiner*—Nay Tun
(74) *Attorney, Agent, or Firm*—Fitzpatrick, Cella, Harper & Scinto

(57) ABSTRACT

An apparatus for detecting information on an object includes an irradiating unit, a detecting unit, and an information-obtaining unit. The irradiating unit irradiates the object with electromagnetic waves as a rectangular shaped beam. The electromagnetic waves include a frequency component in (or range of) at least part of a frequency region of 30 GHz to 30 THz, and have variations in magnitude at intervals of $10^{-11}$ seconds or more or a temporally constant magnitude. The detecting unit detects the electromagnetic waves transmitted or reflected by the object through interaction therebetween. The information-obtaining unit obtains information on the object from information on the electromagnetic waves detected by the detecting unit.

10 Claims, 8 Drawing Sheets

U.S. PATENT DOCUMENTS

| | | |
|---|---|---|
| 2006/0214176 A1 | 9/2006 | Ouchi et al. |
| 2006/0227340 A1 | 10/2006 | Shioda et al. |
| 2006/0244629 A1 | 11/2006 | Miyazaki et al. |
| 2007/0030115 A1 | 2/2007 | Itsuji et al. |
| 2007/0215808 A1 | 9/2007 | Sekiguchi et al. |
| 2007/0229094 A1 | 10/2007 | Kasai et al. |
| 2007/0235718 A1 | 10/2007 | Kasai et al. |
| 2007/0257194 A1 * | 11/2007 | Mueller .................. 250/341.8 |

OTHER PUBLICATIONS

U.S. Appl. No. 10/587,261, filed Jul. 26, 2006, Inventor(s) Sekiguchi, et al.

U.S. Appl. No. 11/833,781, filed Aug. 3, 2007 (GAU 2828) Inventor(s) Ouchi, et al.

U.S. Appl. No. 11/727,588, filed Mar. 27, 2007, (GAU 1753), Inventor(s) Ouchi, et al.

U.S. Appl. No. 11/751,517, filed May 21, 2007, (GAU 2618), Inventor(s) Itsuji, et al.

* cited by examiner

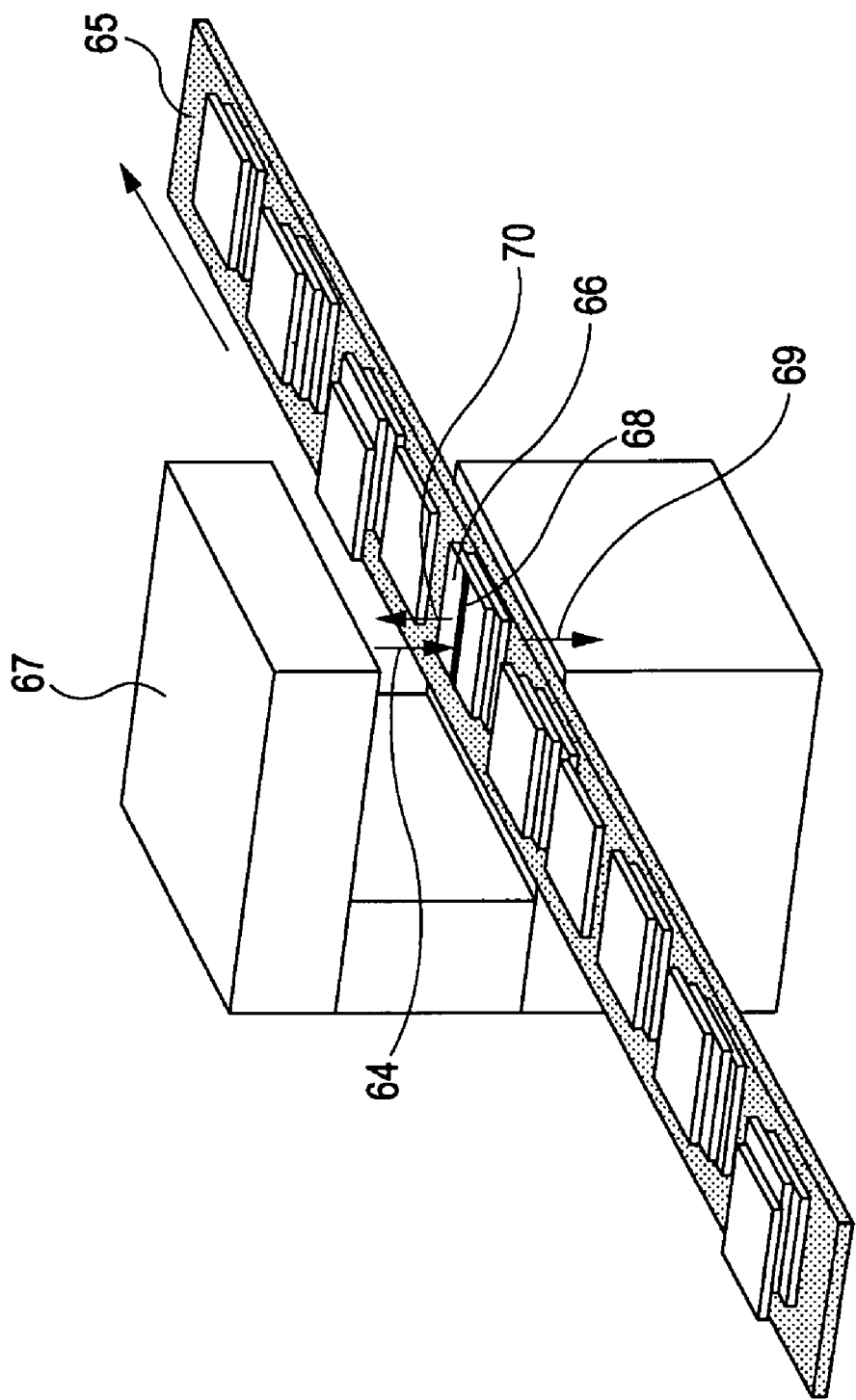

APPARATUS FOR DETECTING INFORMATION ON OBJECT

BACKGROUND OF THE INVENTION

1. Field of the Invention

The present invention relates to apparatuses and methods for detecting information on objects (samples), including image-obtaining apparatuses for observing the properties and shapes of objects using electromagnetic waves with high frequencies, mainly from millimeter waves to terahertz waves (30 GHz to 30 THz).

2. Description of the Related Art

Nondestructive sensing technology based on electromagnetic waves ranging from millimeter waves to terahertz (THz) waves (30 GHz to 30 THz, hereinafter simply referred to as THz waves or THz light) has recently been developed. The field of applications for electromagnetic waves in this frequency band under development includes: imaging technology for providing a safe alternative to radioscopy; spectroscopy for examining the properties of a substance, such as bound states, by determining the absorption spectrum and complex dielectric constant of the substance; analysis of biomolecules; and evaluation of carrier density and mobility.

U.S. Pat. No. 5,789,750 discusses a photoconductive switching element as an example of a suitable THz generator. This photoconductive switching element includes a substrate having a photoconductive film deposited thereon and an antenna serving as an electrode. Examples of frequently used photoconductive films include a radiation-damaged silicon film deposited on a sapphire substrate and a low-temperature-grown GaAs (LT-GaAs) film deposited on a GaAs substrate.

U.S. Pat. No. 5,710,430 discusses a method for obtaining a THz image by two-dimensionally scanning an object with photoconductive switching elements disposed on the transmitter and detector sides thereof, as shown in FIG. 9. According to this publication, the dispersion/absorption properties of an object for THz waves can be used to obtain an optically unobservable internal image such as an interconnection pattern inside an IC chip.

This scanning method, however, takes much time to obtain a two-dimensional image. Japanese Patent Laid-Open No. 2004-85359 discusses a method for inspecting an object at high speed by simultaneously irradiating the object with THz waves over a one-dimensional region. According to this publication, THz pulse light (generally having a pulse width of 3 ps or less) is shaped into a one-dimensional beam using, for example, a parabolic cylindrical mirror for high-speed transmission/reflection spectroscopy of objects.

Detection by the methods discussed in U.S. Pat. No. 5,710,430 and Japanese Patent Laid-Open No. 2004-85359 involves excitation (pumping) of THz pulse waves with a femtosecond laser and gating with a probe laser. These methods require a complicated, less flexible optical system to synchronize pumping light and probe light. In addition, a high signal-to-noise (S/N) ratio is difficult to achieve because the power of THz waves generated by photoconductive switching elements is generally on the order of submicrowatts. To increase sensitivity, therefore, the speed at which signals are obtained should typically be reduced, and accordingly the speed at which images are obtained is limited. Furthermore, the resolution of pulse light is limited because the light is typically susceptible to wavelength dispersion. The above methods also have limited applications because they generally require a large, expensive apparatus with large power consumption, typified by a high-power femtosecond laser. This is a bottleneck in popularizing the use of THz imaging in industry.

In addition, THz waves used in known methods for obtaining images often have a circular or oval Gaussian intensity distribution. Some THz generators generate THz waves with a multipeaked distribution, not even a Gaussian distribution. When pixels are simultaneously obtained, such an intensity distribution tends to degrade peripheral image quality.

SUMMARY OF THE INVENTION

An apparatus for detecting information on an object according to the present invention includes an irradiating unit, a detecting unit, and an information-obtaining unit. The irradiating unit irradiates the object with electromagnetic waves as a rectangular shaped beam. The electromagnetic waves include a frequency component in (or range of) at least part of a frequency region of 30 GHz to 30 THz, and have variations in magnitude at intervals of $10^{-11}$ seconds or more or a temporally constant magnitude. The detecting unit detects the electromagnetic waves transmitted or reflected by the object through interaction therebetween. The information-obtaining unit obtains information on the object from information on the electromagnetic waves detected by the detecting unit.

In addition, a method for detecting information on an object according to the present invention includes an irradiating step, a detecting step, and an information-obtaining step. The irradiating step includes irradiating the object with electromagnetic waves as a rectangular shaped beam. The electromagnetic waves include a frequency component in (or range of) at least part of a frequency region of 30 GHz to 30 THz, and have variations in magnitude at intervals of $10^{-11}$ seconds or more or a temporally constant magnitude. The detecting unit includes detecting the electromagnetic waves transmitted or reflected by the object through interaction therebetween. The information-obtaining step includes obtaining information on the object from information on the electromagnetic waves detected in the detecting step.

In the apparatus and method according to the present invention, the rectangular shaped beam can be defined as a generic term referring to beams of a beam pattern having two axes (typically having a major axis and a minor axis, although the two axes can have the same length), and not referring to, for example, circular Gaussian distribution beams generated by a generating unit. That is, the rectangular shaped beam shape according to the present invention can be exemplified by a general rectangular shape shown in FIG. 8A, an elongated strip shape shown in FIG. 8B, and an elongated oval shape shown in FIG. 8C. In addition to general rectangles, including squares, and elongated oval shapes, examples of the rectangular shaped beam shape can also include rhombuses, trapezoids, and other various polygons and shapes having a curve, if they can be roughly regarded as a rectangular pattern having two axes. For example, any rectangular beam shape can be used which allows the use of a method of combining regions where images are obtained by simultaneously detecting electromagnetic waves on an array detector to obtain a whole image.

According to the present invention, an object is irradiated with the electromagnetic waves described above as a rectangular shaped beam. Information (such as transmission images or reflection images) on the object can thus be obtained at a relatively high speed without decreasing accuracy (such as image resolution).

Further features of the present invention will become apparent from the following description of embodiments with reference to the attached drawings.

BRIEF DESCRIPTION OF THE DRAWINGS

FIG. 4 is a perspective view of an example of an apparatus for detecting or inspecting moving samples according to the present invention.

DESCRIPTION OF THE EMBODIMENTS

Figure 1:
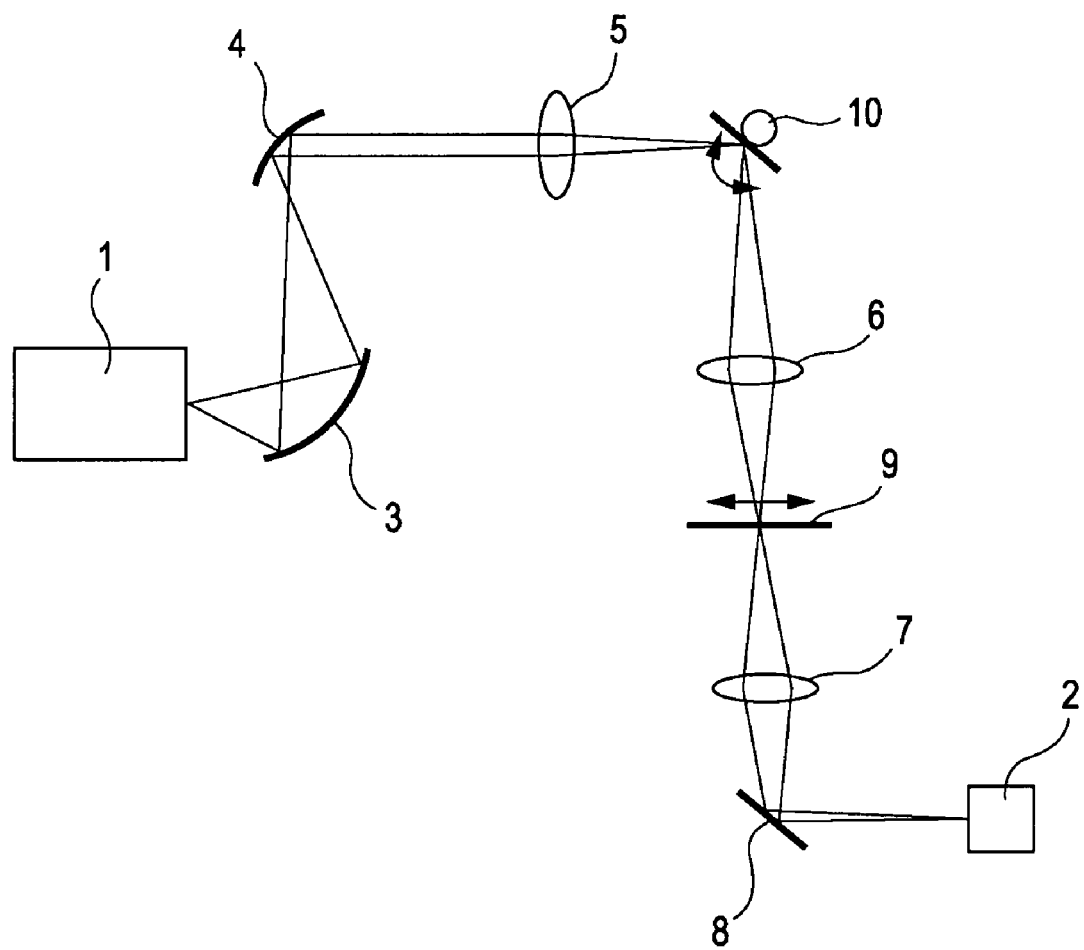
FIG. 1 is a diagram of a detecting apparatus or image-obtaining apparatus according to a first embodiment of the present invention.

Embodiments of the present invention will now be described. In the embodiments of the present invention, a coherent THz generator (generating unit) with a relatively high power (on the order of microwatts or more) can be used instead of a THz generator with a femtosecond laser for excitation. A converting unit converts THz waves output from the THz generator into a rectangular shaped beam before irradiation of an object (sample). A relative-position-changing unit changes the relative positions of the rectangular shaped beam of the THz waves and the sample to scan the sample with the beam while an electromagnetic wave array detector (detecting unit) detects the THz waves from the sample. An information-obtaining unit obtains an image of the sample in a target region from information on the detected THz waves. Thus, pixels are obtained using the rectangular shaped beam by the array detector, which corresponds to the rectangular shaped beam, and regions including the pixels are combined by the information-obtaining unit to obtain a single image of the sample.

The THz generator used can be a coherent THz light source such as a semiconductor oscillator (for example, a quantum cascade laser or a resonant tunneling diode), a backward wave oscillator (BWO), a Gunn diode and its harmonic generator, and a parametric oscillator including a nonlinear crystal such as lithium niobate (LN). The output power of the THz generator is typically several microwatts to hundreds of milliwatts. Also, an incoherent light source such as a heater, an incandescent lamp, or a mercury lamp can be used in combination with a filter for extracting electromagnetic waves in the THz range. In comparison with THz sources with a femtosecond laser for excitation, the light sources described above are characterized in that they have substantially no variations in output power (continuous wave (CW) operation) or only variations at intervals of the order of milliseconds to nanoseconds, that is, they have substantially no variations at intervals less than 10 ps.

The detector used can be, for example, a pyroelectric detector including a ferroelectric crystal, an MEMS-based heat detector, a Schottky diode, a resonant tunneling diode, or a semiconductor quantum detector, any of which can be used in an arrayed form. Electromagnetic waves output from the THz generator are converted into a beam using, for example, a lens or a parabolic mirror. The beam is in turn converted into a rectangular shaped beam using, for example, a cylindrical lens or a parabolic cylindrical mirror. If the intensity distribution of the beam is converted from a Gaussian distribution to a rectangular shaped distribution using, for example, a diffuser, an image-obtaining unit can obtain images without unevenness.

The specific rectangular pattern used is selected according to S/N ratio, which depends on the generator, the detector, and the sample. If the S/N ratio is sufficient, the THz waves are converted into a rectangular or square shape, and a two-dimensional array detector is selected to obtain two-dimensional image regions which are combined into a whole image. If the S/N ratio is insufficient, a whole image can be obtained by combining one-dimensional images obtained with the THz waves converted into a strip-like beam or an elongated oval beam having a one-dimensional linear shape to increase the power density thereof.

The method described above can virtually eliminate the need for synchronization of pumping light and probe light to facilitate adjustment of an optical system and reduce the overall size thereof. An additional system such as a delay system or an interference system (see third and fourth embodiments described later) can be provided upstream of the detector to obtain information on, for example, the constituent distribution of the sample as phase information. Images can be obtained using waves transmitted through the sample and/or waves reflected by the sample. The relative-position-changing unit used for scanning is exemplified by a galvanometer mirror for scanning with a light axis and a scanning stage or a belt conveyor for moving a sample. The relative-position-changing unit includes a movable mirror for changing the reflection direction of the electromagnetic waves in the irradiating unit or moves the object in one axial direction to change the relative positions of the irradiating electromagnetic waves and the object. The scanning can be efficiently performed by relatively moving the electromagnetic waves and the object in a direction across the major axis of the beam pattern of the THz waves, particularly, in a direction substantially perpendicular to the major axis.

This method will be further described with reference to FIGS. 1 and 2. In FIG. 1, a THz generator 1 is a quantum cascade laser that outputs a continuous wave with a frequency of 2.9 THz and a power of 10 mW when cooled to a liquid-nitrogen temperature and supplied with current. This output is converted into a collimated beam with a diameter of about 3 cm using two parabolic mirrors 3 and 4. A cylindrical lens 5 focuses a component of the beam parallel to the drawings as shown in FIG. 1, while maintaining the collimated shape of a component of the beam perpendicular to the drawings. The beam is reflected by the galvanometer mirror 10 and is focused again onto a surface of a sample 9 by a cylindrical lens 6. The cylindrical lens 6 converts the beam into a strip-like beam with a length of about 3 cm in the direction perpendicular to the drawings.

After passing through the sample 9, the beam is focused again by a cylindrical lens 7 and is detected by a one-dimensional array THz detector 2 via a reflective mirror 8, for example. In practice, a two-dimensional image can be obtained using part of a two-dimensional array pyroelectric detector by signal detection synchronized with the movement of the galvanometer mirror 10. The lenses 6 and 7 can be arranged such that the focal points thereof are positioned on the surface of the galvanometer mirror 10, the surface of the sample 9, and a detection surface of the two-dimensional array pyroelectric detector, as shown in FIG. 1. The position of the beam focused onto the detection surface can be fixed or moved with the movement of the galvanometer mirror 10.

Figure 2:
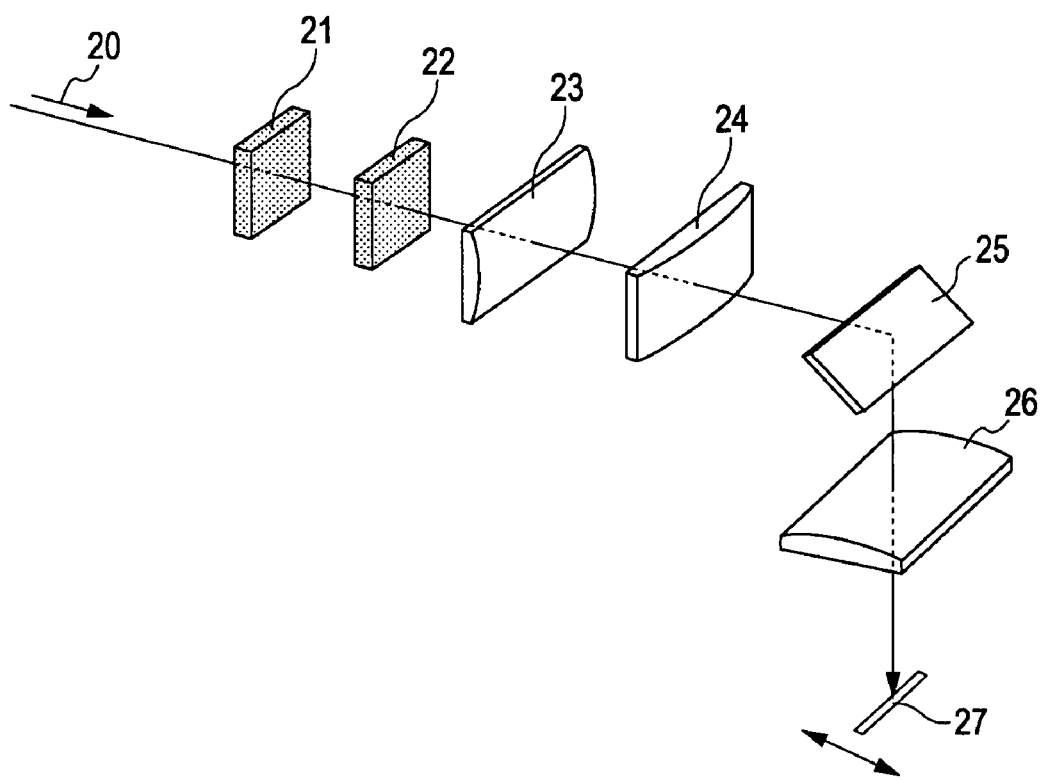
FIG. 2 is a perspective view illustrating an example of a method for forming a rectangular shaped beam.

An optical system shown in FIG. 2 can be used to form a strip-like beam with uniform THz intensity. THz waves 20 converted into a collimated beam with a diameter of about 3 cm by the parabolic mirror 4 passes through fly-eye lenses 21 and 22 corresponding to two orthogonal directions. These fly-eye lenses 21 and 22 convert the intensity distribution of the beam from a Gaussian distribution to a rectangular distribution. The beam is then converted into a strip-like beam with a width of 1 mm and a length of 2.5 cm by cylindrical convex lenses 23 and 24, is reflected by a galvanometer mirror 25, and is projected onto the surface of the sample 9 in a beam shape 27 by a cylindrical convex lens 26. Although this optical system is a lens system, a similar system can also be constructed using parabolic cylindrical mirrors instead of cylindrical lenses as a reflective mirror system, as described above, or using diffusers instead of fly-eye lenses.

The aspect ratio of the beam is determined according to the S/N ratio, which depends on the generator 1, the detector 2, and the sample 9, as described above. For example, it can be assumed that the array THz detector 2 can ensure an S/N ratio of 2 or more with a beam diameter of 8 mm for a collimated circular beam with a spatially uniform intensity distribution. If the imaging spatial resolution is 0.3 mm, a strip-like beam with a width of 1 mm can be used to make allowance. The length of the strip-like beam along the major axis thereof can be determined so that the beam has substantially the same total THz power after beam conversion. In this case, the length of the beam along the major axis thereof is determined to be $\pi(8/2)^2/1$, namely, 50 mm, under the assumption that the strip-like beam has a substantially uniform distribution after beam conversion. Hence, a strip-like beam with a width of 1 mm and a length of 50 mm can be used for detection. In practice, the effective length of the beam along the major axis thereof is determined to be 25 mm in the example described above with consideration given to loss due to beam conversion and peripheral distortion. The sample 9 can be irradiated with a strip-like beam having a length of 25 mm along the major axis thereof with uniform intensity, to obtain images without unevenness. The intensity distribution of the beam can also be converted into a rectangular distribution only along the major axis thereof, with a Gaussian distribution remaining along the width of the beam (along the minor axis thereof). In this case, images can be formed after correction by the image-obtaining unit with the above conditions stored in advance. If the length of the strip-like beam along the major axis thereof is different from the width of a photosensitive portion of the array detector 2, the length of the beam along the major axis thereof can be reduced using, for example, a cylindrical lens (not shown).

The aspect ratio can be further increased (i.e., more elongated) for larger imaging widths by increasing the intensity of the THz waves or the sensitivity of the THz detector 2, although such an apparatus would most likely be costly. That is, there is typically a trade-off between imaging speed and system cost, and the optimum design should be selected according to applications.

In the system shown in FIG. 2, accordingly, a two-dimensional THz image with a size of 2.5 cm by 5 cm can be obtained by shifting the position of the beam projected onto the sample 9 in the arrow direction by a distance of 5 cm using the galvanometer mirror 25. A method for further increasing the image area and a method for imaging the physical property distribution of an object by obtaining information on the phase shift of electromagnetic waves from the object, for example, will be described with reference to the embodiments below.

As described above, a transmission or reflection THz image of an object can be obtained at high resolution and high speed using a simpler and smaller apparatus. This THz imaging apparatus is seen to have a wide range of applications as an industrial product, including inspection of articles in airports, public transportation, and distribution centers; defect inspection of products at production sites; and pathological inspection at medical institutions.

First Embodiment

A first embodiment of the present invention will be described with reference to FIGS. 1 and 2. In the first embodiment of the present invention, a sample 9 is subjected to transmission imaging. In the first embodiment, electromagnetic waves output from the THz generator 1 are converted into a strip-like beam for increased S/N ratio, and a one-dimensional image is obtained by the THz detector 2. A two-dimensional image of the sample 9 is obtained by combining one-dimensional images obtained by scanning the sample 9 with the strip-like beam by moving the galvanometer mirror 10 in a rotational direction shown in FIG. 1. This fundamental system is as described above.

The array THz detector 2 used in this embodiment is a pyroelectric detector including a two-dimensional $LiTaO_3$ array with 128 columns and 128 rows. The pixel pitch of the array is 100 µm. Although the two-dimensional array is used, one-dimensional images are obtained by image processing. The one-dimensional range of pixels can be increased by irradiation with a one-dimensional beam along a diagonal line of the detector 2. Because the length of the strip-like beam along the major axis thereof is larger than the size of the detector 2 (about 12.5 mm), the size of the beam is reduced using, for example, a cylindrical lens (not shown) so that the beam can enter the detector 2, as described above.

Although a strip-like beam can be formed using the simple system shown in FIG. 1, another lens system as shown in FIG. 2 can be used in combination to form a strip-like beam with a more uniform intensity distribution. As described above, such a combined system can provide a sharp image without unevenness from center to periphery. Examples of the material used for lenses include: resins such as polyethylene, fluoropolymers (typified by Teflon®), and polyolefins; ceramics such as alumina and AlN; and other materials such as high-resistivity silicon and quartz. These materials exhibit less attenuation for THz waves.

The apparatus described above can obtain THz transmission images of, for example, plastic dolls, tablets in a styrofoam box, and chocolate products with rough surfaces in a paper box. The apparatus is seen to enable, for example, inspection for the presence or shape of articles packed in boxes at factories and distribution centers without opening the boxes, inspection for tablets hidden in baggage, and inspection for surface shapes and imprintings.

The THz generator 1 used in this embodiment is a semiconductor quantum cascade THz laser chip of several millimeters square. Even though this laser requires a device for cooling it to 100 K or lower, the apparatus according to this embodiment is significantly smaller and consumes less power than known systems including a femtosecond laser.

Second Embodiment

Figure 3:
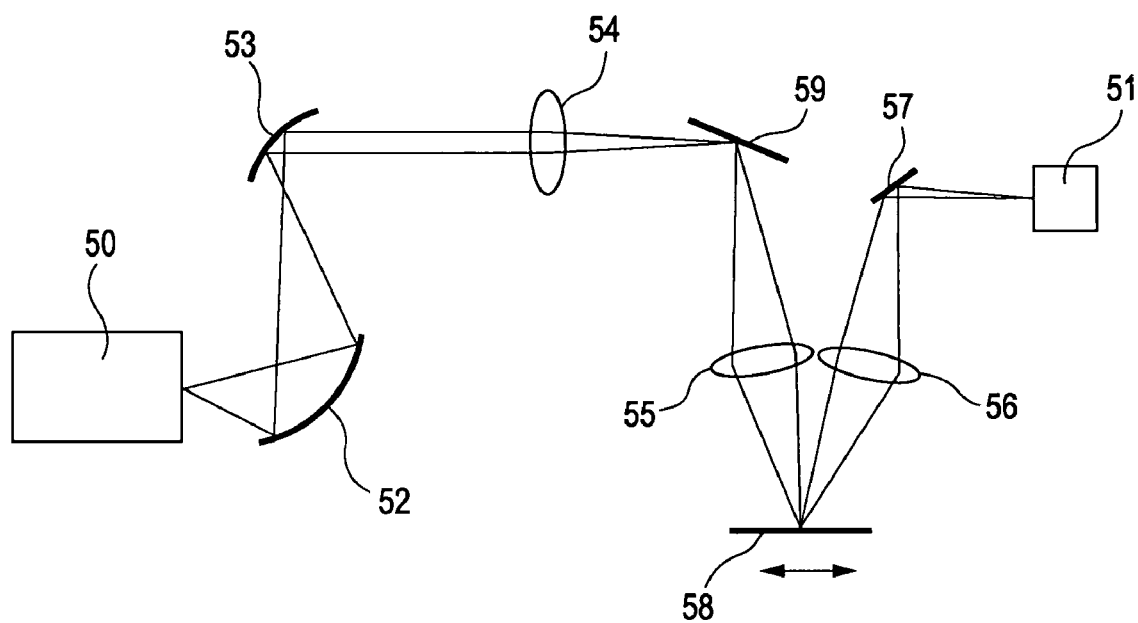
FIG. 3 is a diagram of a detecting apparatus or image-obtaining apparatus according to a second embodiment of the present invention.

A second embodiment of the present invention will be described. In the second embodiment of the present invention, as shown in FIG. 3, imaging is performed by detecting THz waves reflected by a sample 58. The system used for irradiation with THz waves is substantially the same as used in the first embodiment. Basically, the reflected waves are obliquely incident on the sample 58 for ease of detection. In this embodiment, the irradiation system includes a THz generator 50, two parabolic mirrors 52 and 53, and cylindrical lenses 54 and 55. A beam focused by the cylindrical lens 54 is reflected by a galvanometer mirror 59. The THz waves reflected by the sample 58 are made incident on an array THz detector 51, similar to that used in the first embodiment, by a cylindrical lens 56 and a reflective mirror 57, so that an image is obtained.

This system can be used for a THz inspecting apparatus 67 shown in FIG. 4 to inspect samples 66 being conveyed by a belt conveyor 65. This THz inspecting apparatus 67 irradiates the samples 66 with, for example, THz waves 64 from thereabove in the form of a strip-like beam 68, and an upper detector (not shown) detects reflected THz waves 70 to obtain an image. Alternatively, as described in the first embodiment, a lower detector (not shown) can be disposed to detect transmitted THz waves 69 and obtain a transmission image. An image can also be obtained using a fixed mirror, rather than using a movable mirror, in synchronization with the movement of the belt conveyor 65 by increasing the THz wave output and expanding the strip-like beam 68 according to the width of the samples 66. This is seen to allow simplification of the optical system.

Figure 5A:
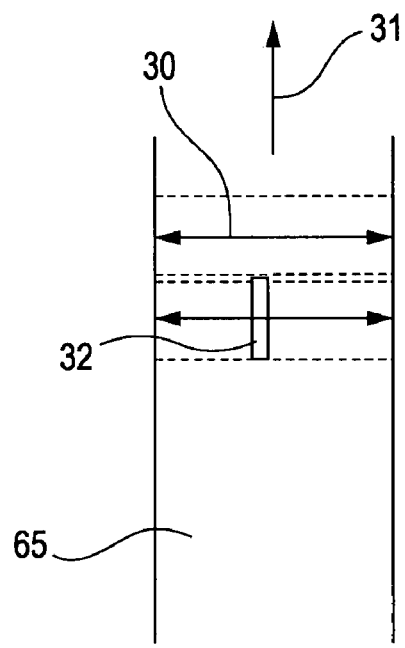
FIGS. 5A and 5B are plan views illustrating examples of methods for image scanning according to the present invention.
Figure 5B:
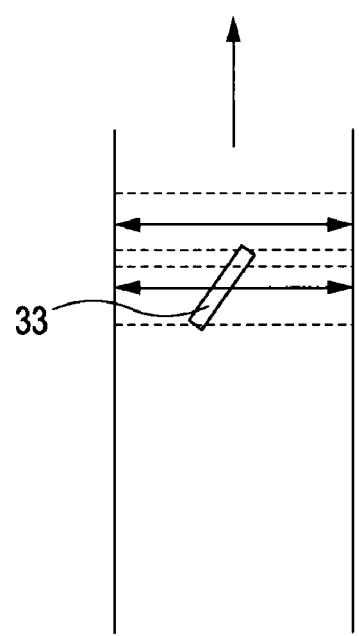

If the samples 66 have a large width that typically cannot be covered by beam expansion, beam scanning and sample movement can be used in combination, as shown in FIGS. 5A and 5B. In FIG. 5A, wide samples can be inspected by moving a strip-like or rectangular shaped beam 32 in a direction perpendicular to the movement direction of the belt conveyor 65, as indicated by arrows 30, using a movable mirror while conveying the samples in a direction indicated by an arrow 31 in synchronization. In FIG. 5B, wide samples can also be scanned with a strip-like beam 33 inclined with respect to the movement direction of the samples in an overlapping manner to increase the effective number of pixels of a detector having a predetermined number of pixels. If the belt conveyor 65 is continuously moved, the samples can be scanned in a direction relatively perpendicular to the movement direction of the belt conveyor 65, that is, in a direction inclined with respect to the longitudinal direction of the belt conveyor 65 in a static system.

For example, this inspecting/detecting apparatus can be used for safe, quick inspection of packaged articles at distribution centers and inspection of baggage for knives, guns, and banned substances in public transportation.

Third Embodiment

A third embodiment of the present invention will be described. In the third embodiment of the present invention, the type of object is roughly identified by detecting not only the transmittance or reflectance distribution of the object for THz waves, but also the phase shift distribution thereof, which depends on variations in dielectric constant. This can be achieved using an optical system including a delay optical system shown in FIG. 6. The transmission optical system used for a sample 94 in this embodiment is substantially the same as used in the first embodiment. That is, the irradiation system includes a THz generator 80, two parabolic mirrors 82 and 83, and cylindrical lenses 85 and 86. A beam focused by the cylindrical lens 85 is reflected by a galvanometer mirror 93. THz waves transmitted through the sample 94 are made incident on an array THz detector 81, similar to that used in the first embodiment, by a cylindrical lens 87 and a reflective mirror 88, so that an image is obtained.

In this embodiment, part of the THz waves is made incident on a delay optical system 90 including two mirrors by a beam splitter 84 disposed in front of the cylindrical lens 85 and is combined with the transmitted THz waves using a mirror 91, a parabolic mirror 92, and a beam splitter 89. The interfering THz light is made incident on the THz detector 81, which includes a Schottky diode array. This system can obtain an image with signals varying with the phase shift distribution of the sample 94. A wire-grid polarizer can be used as the beam splitter 84, and any branching ratio can be selected by changing a grid angle with respect to the polarization direction of the THz waves.

Figure 6:
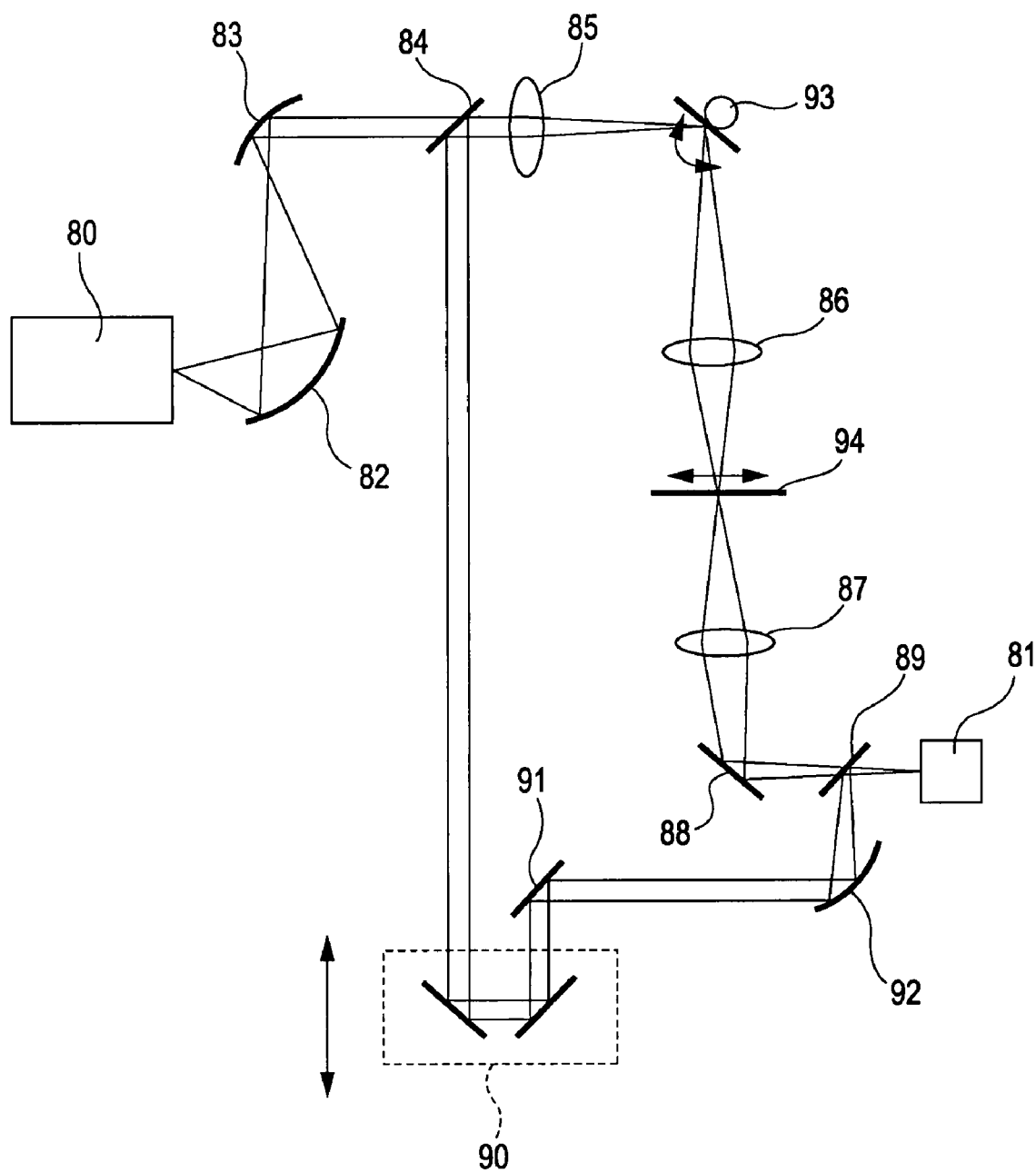
FIG. 6 is a diagram of a detecting apparatus or image-obtaining apparatus according to a third embodiment of the present invention.

Accordingly, the system shown in FIG. 6 can provide image signals corresponding to variations in dielectric constant, even if the sample 94 exhibits little difference in transmittance. In addition, the material of the sample 94 can be identified if intensity variations corresponding to dielectric constant are stored in advance for comparison. Furthermore, a sharper image of an irregular shape can be obtained because phase shifts corresponding to thickness occur even if the sample 94 has a uniform dielectric constant.

Fourth Embodiment

Figure 7:
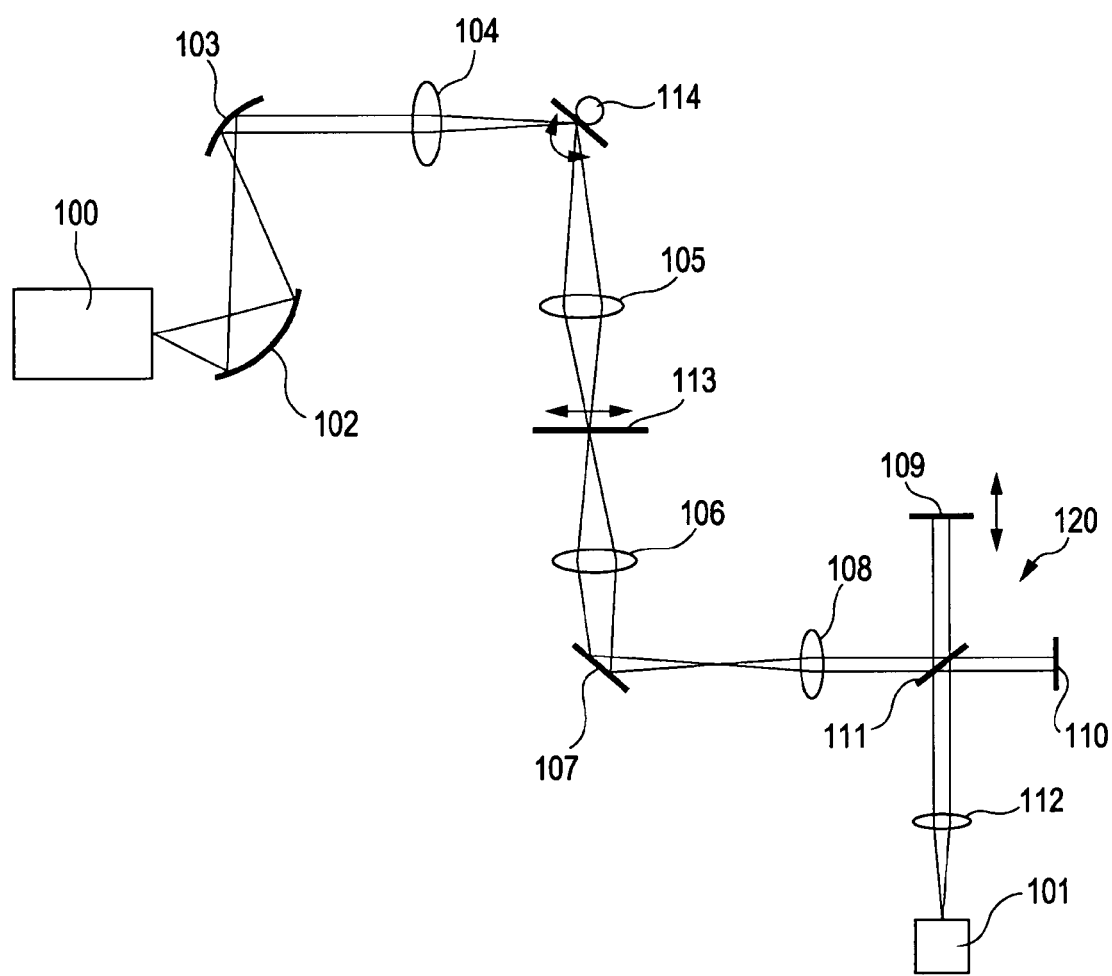
FIG. 7 is a diagram of a detecting apparatus or image-obtaining apparatus according to a fourth embodiment of the present invention.
Figure 8A:
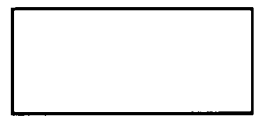
FIGS. 8A, 8B, and 8C are diagrams of examples of rectangular shaped beams according to the present invention.
Figure 8B:
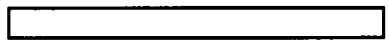
Figure 8C:
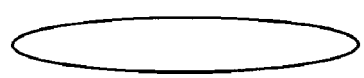
Figure 9:
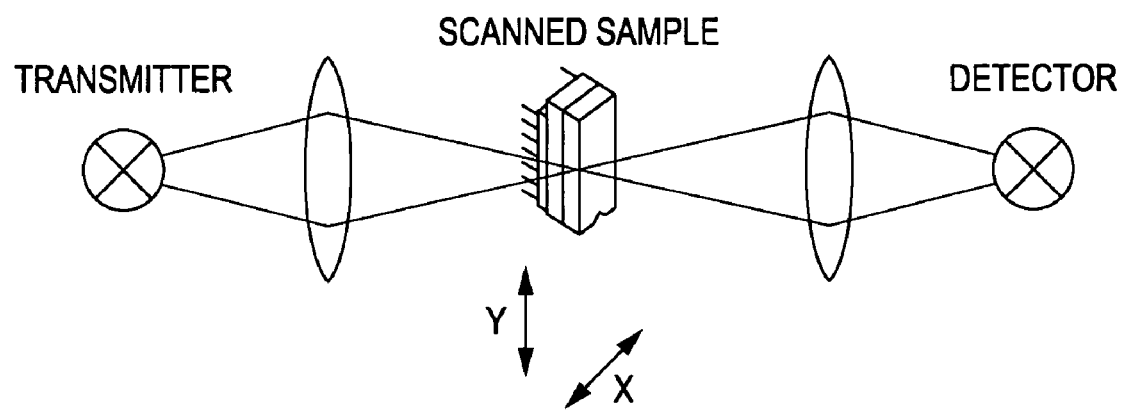
FIG. 9 is a diagram of an example of a known image-obtaining apparatus.

A fourth embodiment of the present invention will be described. The fourth embodiment of the present invention provides effects similar to those of the third embodiment, including detection of phase shift distribution. In this embodiment, particularly, a Michelson interferometer 120 is used, as shown in FIG. 7. The transmission optical system used in this embodiment is substantially the same as used in the first embodiment, although a reflection optical system can also be used. The irradiation system used in this embodiment includes a THz generator 100, two parabolic mirrors 102 and 103, and cylindrical lenses 104 and 105. A beam focused by the cylindrical lens 104 is reflected by a galvanometer mirror 114. THz waves transmitted through a sample 113 pass through a cylindrical lens 106 and are reflected by a reflective mirror 107.

The structure of the Michelson interferometer 120 used in this embodiment will be described. The transmitted THz waves reflected by the reflective mirror 107 are collimated by a cylindrical lens 108 and are split into two beams by a beam splitter 111. These two beams are reflected by two respective mirrors 109 and 110, are combined with each other, and are focused again onto a detection surface of a THz detector 101 by a cylindrical lens 112. The phase shift distribution of the THz waves is detected by controlling the interference state thereof using the movable mirror 109. A higher S/N ratio can be achieved according to a synchronization detection technique by applying minute vibrations to the movable mirror 109. In this embodiment, an image corresponding to the type of material can be obtained as in the third embodiment.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-037765 filed Feb. 15, 2006, which is hereby incorporated by reference herein in its entirety.

What is claimed is:

1. An imaging apparatus comprising:
   an irradiating unit comprising:
      a generating unit for generating electromagnetic waves having a frequency range of at least part of a frequency region of 30 GHz to 30 THz; and
      a converting unit for converting an intensity distribution of the electromagnetic waves generated by the generating unit into a rectangular distribution;
   wherein the irradiating unit irradiates an object with the electromagnetic waves having the intensity distribution of the rectangular distribution;
   the imaging apparatus further comprising:
   an array detecting unit for detecting, by a plurality of pixels, the electromagnetic waves having the intensity distribution of the rectangular distribution and transmitted through or reflected by the object;
   an irradiated-position-changing unit for changing an irradiated position of the object that is irradiated with the electromagnetic waves having the intensity distribution of the rectangular distribution; and
   an image-obtaining unit for obtaining a plurality of images of the object corresponding to the rectangular distribution from the electromagnetic waves detected by the array detecting unit with the irradiated position being changed by the irradiated-position-changing unit, and for obtaining a whole image of the object from the plurality of images.

2. The imaging apparatus according to claim 1, wherein
   the generating unit generates the electromagnetic waves having variations in magnitude at intervals of $10^{-11}$ seconds or more, or a constant magnitude; and
   the converting unit includes a cylindrical lens or a parabolic cylindrical mirror, and a fly-eye lens or a diffuser.

3. The imagine apparatus according to claim 2,
   wherein the fly-eye lens or the diffuser is arranged such that the intensity distribution of the electromagnetic waves generated by the generating unit is converted from a Gaussian distribution to a rectangular distribution, and
   wherein the image-obtaining unit obtains one-dimensional images corresponding to the converted rectangular distribution and combines the images to obtain a two-dimensional image.

4. The imaging apparatus according to claim 1 further comprising;
   a dividing unit for dividing the electromagnetic waves generated by the generating unit;
   a delay optical unit for delaying electromagnetic waves not to be interacted with the object among the electromagnetic waves divided by the dividing unit; and
   a combining unit for combining the electromagnetic waves that have interacted with the object and electromagnetic waves that have not interacted with the object,
   wherein the image-obtaining unit obtains a phase shift distribution of the electromagnetic waves that have interacted with the object as an image.

5. The imaging apparatus according to claim 1, further comprising;
   a dividing and combining unit for dividing electromagnetic waves that have interacted with the object;
   a reflecting mirror for reflecting the electromagnetic waves divided by the dividing and combining unit; and
   a movable mirror for adjusting a transmission distance of electromagnetic waves that are different from the electromagnetic waves reflected by the reflecting mirror among the electromagnetic waves divided by the dividing and combining unit,
   wherein the dividing and combining unit combines the electromagnetic waves reflected by the reflecting mirror and the electromagnetic waves reflected by the movable mirror, and
   wherein the image-obtaining unit obtains a phase shift distribution of the electromagnetic waves that have interacted with the object as an image.

6. The imaging apparatus according to claim 1, wherein the generating unit comprises a coherent light source that causes oscillation at any single frequency in the frequency region of 30 GHz to 30 THz.

7. The imagine apparatus according to claim 1, wherein the irradiated-position-changing unit comprises a movable mirror for changing a reflection direction of the electromagnetic waves generated by the generating unit.

8. The imaging apparatus according to claim 1, wherein the irradiated-position-changing unit moves the object to change the irradiated position.

9. An imaging apparatus for obtaining image information by using terahertz electromagnetic waves, comprising:
   an irradiating unit comprising;
   a generating unit for generating coherent terahertz electromagnetic waves;
   a first converting unit for converting an intensity distribution of the coherent terahertz electromagnetic waves into a rectangular distribution;
   a second converting unit for converting a beam shape of the coherent terahertz electromagnetic waves into a rectangular shape;
   wherein the irradiating unit irradiates an object with the rectangular shaped beam formed by the first and second converting units;
   the imaging apparatus further comprising:
   an array detecting unit comprising a plurality of detecting units for respectively detecting a spatial intensity in each of a plurality of regions in the rectangular shape which is a beam shape of the rectangular shaped beam transmitted through or reflected by the object; and
   an image information obtaining unit for obtaining image information on a region of the object irradiated with the rectangular shaped beam by using the spatial intensity in each of the plurality of regions which is detected by the array detecting means.

10. The imaging apparatus according to claim 9, further comprising an irradiated-position-changing unit for changing an irradiated position of the object that is irradiated with the rectangular shaped beam formed by the first and second converting units
   wherein the image information obtaining unit obtains image information at each of a plurality of irradiated positions, and
   wherein the image information corresponds to the spatial intensity distribution in the rectangular shape of the rectangular shaped beam which is detected by the array detecting unit.

* * * * *